(12) United States Patent
Wang et al.

(10) Patent No.: US 8,501,245 B2
(45) Date of Patent: Aug. 6, 2013

(54) SELECTIVELY INHIBITING ESTROGEN PRODUCTION AND PROVIDING ESTROGENIC EFFECTS IN THE HUMAN BODY

(75) Inventors: Mian Ying Wang, Rockford, IL (US);
Chen Xing Su, West Jordan, UT (US);
Afa Kehaati Palu, Orem, UT (US);
Bing-Nan Zhou, Pleasant Grove, UT (US); Brett Justin West, Orem, UT (US); Johannes Joseph Westendorf, Bremin (DE); Claude Jarakae Jensen, Cedar Hills, UT (US); Stephen Paul Story, Alpine, UT (US)

(73) Assignee: Morinda, Inc., Provo, UT (US)

(*) Notice: Subject to any disclaimer, the term of this patent is extended or adjusted under 35 U.S.C. 154(b) by 194 days.

(21) Appl. No.: 10/808,872

(22) Filed: Mar. 24, 2004

(65) Prior Publication Data
US 2004/0224038 A1 Nov. 11, 2004

Related U.S. Application Data

(63) Continuation-in-part of application No. 10/396,868, filed on Mar. 25, 2003, now abandoned, which is a continuation-in-part of application No. 10/286,167, filed on Nov. 1, 2002, now Pat. No. 6,855,345, application No. 10/808,872, which is a continuation-in-part of application No. 10/285,359, filed on Oct. 31, 2002, now Pat. No. 7,033,624, which is a continuation-in-part of application No. 10/006,014, filed on Dec. 4, 2001, now abandoned.

(60) Provisional application No. 60/458,353, filed on Mar. 28, 2003, provisional application No. 60/335,313, filed on Nov. 2, 2001, provisional application No. 60/251,416, filed on Dec. 5, 2000.

(51) Int. Cl.
*A61K 36/00* (2006.01)

(52) U.S. Cl.
USPC .......................................... 424/725

(58) Field of Classification Search
USPC .......................................... 424/725
See application file for complete search history.

(56) References Cited

U.S. PATENT DOCUMENTS

| 5,708,038 A * | 1/1998 | Davis ............................ 514/783 |
| 6,340,703 B1 * | 1/2002 | Kelly ............................ 514/456 |
| 2006/0099690 A1 * | 5/2006 | Chang et al. .................... 435/75 |

FOREIGN PATENT DOCUMENTS

WO WO 9307901 A1 * 4/1993

OTHER PUBLICATIONS

Rosenbloom-Kerzner, I.; Highland Woman Sells 'Miracle' Drug: The Post-Tribune, Gary, Indiana, Jan. 29, 2002 p. B.2 (pp. 1-3 of ProQuest).*
Elkins, R. Hawaiian Noni; 1998, Woodland Publishing, Pleasant Grove, Utah, p. 8.*
Wang et al. *Morinda citrifolia* 9NON0: A Literature Review and Recent Advances in Noni Research; Acta Pharmacol. Sin; Dec. 2002; 23 (12), pp. 1127-1141, pp. 1-18 of internet print-out.*

* cited by examiner

*Primary Examiner* — Patricia Leith
(74) *Attorney, Agent, or Firm* — Michael F. Krieger; Kirton McConkie

(57) ABSTRACT

Implementation is directed to selectively inhibiting estrogen production and providing estrogenic effects in a human body. A dietary supplement includes a processed *Morinda citrifolia* product that is used to inhibit aromatase or aromatase enzymes that function to convert androgens to estrogens, inhibit receptors from binding with estrogen, and reduce and/or regulate estrogen production, as well as reduce the amount of estrogen produced within the body and regulating such production. The dietary supplement further provides estrogenic effects. The present invention methods and compositions effectively function to treat estrogen-dependent cancers, and particularly inhibit, destroy, and reverse the effects of of estrogen-dependent cancerous tumors through the introduction into the body (e.g. ingesting) a safe, pre-determined dosage of a naturaceutical composition formulated with or comprising one or more processed *Morinda citrifolia* products for a safe, pre-determined duration.

7 Claims, 2 Drawing Sheets

SELECTIVELY INHIBITING ESTROGEN PRODUCTION AND PROVIDING ESTROGENIC EFFECTS IN THE HUMAN BODY

RELATED APPLICATIONS

This application is a continuation-in-part of U.S. patent application Ser. No. 10/396,868, filed Mar. 25, 2003, entitled "PREVENTATIVE AND TREATMENT EFFECTS OF *MORINDA CITIRIFOLIA* AS AN AROMATASE INHIBITOR" and claims priority to U.S. Provisional Patent Application Ser. No. 60/458, 353, filed Mar. 28, 2003, entitled "THE POSSIBLE ESTROGENIC EFFECTS OF TAHITIAN NONI PUREE JUICE CONCENTRATE-DRY FORM", both of which are incorporated herein by reference, and this application is a continuation-in-part U.S. application Ser. No. 10/286/167 now U.S. Pat. No. 6,855,345, filed Nov. 1, 2002, which claims priority to U.S. Provisional Application Ser. No. 60/335,313, filed Nov. 2, 2001, and entitled, "Methods for Treating Conditions Related to Diabetes," and this application is a continuation-in-part of U.S. patent application Ser. No. 10/285,359, now U.S. Pat. No. 7,033,624, filed Oct. 31, 2002, entitled "Preventative and Treatment Effects of Morinda Citrifolia on Osteoarthritis and Its Related Conditions" and is a continuation-in-part of U.S. patent application Ser. No. 10/006,014 filed Dec. 4, 2001 now abandoned, entitled "Tahitian Noni Juice On, Cox-1 And Cox-2 And Tahitian Noni Juice As A Selective Cox-2 Inhibitor", which claims priority to U.S. Provisional Patent Application Ser. No. 60/251,416 filed Dec. 5, 2000, entitled "Cox-1 and Cox-2 Inhibition Study on TNJ."

BACKGROUND OF THE INVENTION

1. Field of the Invention

The present invention relates to estrogenic effects in the human body. More particularly, the present invention relates to the utilization of a dietary composition or supplement to selectively inhibit estrogen production and to provide estrogenic effects in the human body, wherein the composition is formulated with one or more processed products from the Indian Mulberry plant, scientifically known as *Morinda citrifolia L.*

2. Background and Related Art

Estrogens or oestrogens are steroid hormones produced chiefly by the ovaries and are responsible for promoting estrus and for the development and maintenance of female sexual characteristics. In humans, oestrogen is formed in the ovary, possibly the adrenal cortex, the testis, and the foetoplacental unit. Estrogens or oestrogens have various functions. For example, they are responsible for the development of the female secondary sex characteristics and during the menstrual cycle they act on the female genitalia to produce an environment suitable for the fertilization, implantation and nutrition of the early embryo.

Estrogen is produced from an enzyme called aromatase, which is part of an enzyme complex known as Cytochrome P450 that exists in different parts of the body, and particularly within several major organs. The aromatase enzyme in the human body is expressed in the placenta, adipose tissues, hair follicles, muscles, bones, liver and the brain. In the brain, aromatase can be found in the anterior and mediobasal hypothalamus.

Aromatase specializes in converting C19 androgens to aromatic C18 estrogenic steroids. However, aromatase also has the ability to metabolize xenobiotics. The ability or function of aromatase to convert adrenal androgen substrates into estrogens accounts for the sole source of estrogen in post-menopausal women. Therefore, inhibitors of the aromatase enzyme are used to treat postmenopausal breast cancer and other estrogen-dependent diseases.

Only recently have aromatase inhibitors begun to be recognized as a viable treatment option for breast cancer and other estrogen-dependent diseases. As such, use of these inhibitors continues to gain momentum. Aromatase inhibitors belong to a family of hormonal treatments that have been shown in the laboratory, as well as in several clinical trials, to produce significant anti-cancerous activity in relation to breast cancer that is discovered in post-menopausal women. Aromatase inhibitors are especially advantageous or effective in cases where a woman exhibits or possesses greater estrogen-sensitivity.

In has been established and is widely believed that more than two thirds of breast cancer cases are considered "estrogen sensitive" because they are able to grow and proliferate throughout the mammary region and beyond. In response, and to prevent this overgrowth, aromatase inhibitors are introduced, which reduce the amount of circulating estrogen in post-menopausal women, thus causing the estrogen-sensitive or estrogen dependant tumors to stop growing and even shrink. Estrogen sensitive cancers are also known as ER+ (estrogen-receptor positive) and are referred to by others as progesterone-receptor positive (PR+).

Cancerous or tumor cells each have receptors (docking places) located on their cell membrane. As estrogen is produced and released into the body, it binds to these cell receptors. Therefore, in determining the efficacy of inhibitory treatments, it is possible to measure each receptor and its binding efficiency with estrogen. This binding efficiency is commonly referred to as "receptor status." Concomitantly, receptor status becomes an invasive part of the prognosis of breast cancer.

Many aromatase inhibitors inhibit the receptors from binding with estrogen, while others inhibit the actual aromatase enzymes that function to convert androgens to estrogens. In addition, aromatase inhibitors lower estrogen more effectively after menopause because in menopause, both ovaries stop producing estrogen. However, that is not to say that no amount of estrogen is produced in the body. The low level of estrogen that is produced after menopause is a result of the aromatase enzymes converting other naturally occurring hormones into estrogen. As such, aromatase inhibitors were developed to effectively prevent aromatase enzymes from being used to produce estrogen. As a result, estrogen levels in the body fall, and estrogen-dependent tumors begin to or are more likely to shrink and digress. In contradistinction, before menopause, estrogen is mainly produced in the ovaries, with only a small amount being produced from the aromatase process. Numerous studies have indicated that aromatase inhibitors do not lower estrogen levels enough in premenopausal women to affect tumor growth.

Currently, there are a very limited number of aromatase inhibitors that are actually in use and that have been approved by the Food and Drug Administration. Some of the more widely used inhibitors are Arimidex®, Aromasin®, and Femara,® which have all gone through several clinical trials. Although effective at performing their intended function of inhibiting the aromatase enzymes, these inhibitors induce numerous undesirable side effects in the patient, thus making their treatment less popular and less desirable. Interestingly enough, these approved treatments for postmenopausal women consist of drugs that block estrogen receptors on the surface of tumor cells and are either reversible or irreversible.

However, their side effects consist of, but are not limited to, sweating, hot flashes, fatigue, appetite changes, headaches, bone pain, chest pain, coughing, shortness of breath, and in some patients, blood clots.

Techniques also exist for the harvesting of estrogens or oestrogens for increasing the level of estrogen located in the human body. Such techniques include harvesting them from the urine of pregnant horses. While this technique is available, a number of side effects exist, including such similar side effects as sweating, hot flashes, fatigue, appetite changes, headaches, bone pain, chest pain, coughing, shortness of breath, and the like. Accordingly, great efforts are being made by research and development groups in hopes to obtain an improved harvesting technique and/or an improved composition that produces a safer estrogen hormone for utilization in the body.

Thus, while techniques currently exist that are used to inhibit estrogen production and to harvest estrogen for utilization in the body, challenges still exist, including such undesirable side effects as sweating, hot flashes, fatigue, appetite changes, headaches, bone pain, chest pain, coughing, shortness of breath, and the like. Accordingly, it would be an improvement in the art to augment or even replace current techniques with other techniques.

SUMMARY OF THE INVENTION

The present invention relates to estrogenic effects in the human body. More particularly, the present invention relates to the utilization of a dietary composition or supplement to selectively inhibit estrogen production and to provide estrogenic effects in the human body, wherein the composition is formulated with one or more processed products from the Indian Mulberry plant, scientifically known as *Morinda citrifolia L.*

Implementation of the present invention takes place in association with a dietary composition or supplement that is processed from a product of the Indian Mulberry plant, scientifically known as *Morinda citrifolia* L. ("*Morinda citrifolia*"). The product of the *Morinda citrifolia* can come from the fruit, leaves, seeds, roots, or any other part of the *Morinda citrifolia*. In one implementation, the dietary supplement includes reconstituted *Morinda citrifolia* fruit juice from pure juice puree of French Polynesia. The supplement may also include other natural juices, such as a natural grape juice concentrate, a natural blueberry juice concentrate, and/or another natural juice concentrate. In one implementation, liquid is extracted from the fruit of the *Morinda citrifolia* and used to create the dietary supplement for consumption. At least one implementation of the dietary supplement is referred to as "Tahitian Noni®" and may be obtained from Morinda, Inc., which has a principal place of business located at 5152 N. Edgewood Dr. #100, Provo, Utah, 84604.

In another implementation, the dietary supplement is processed from the leaves of the *Morinda citrifolia* to produce a dried or powdered dietary supplement, which may be placed, for example, in a tablet form for consumption. In yet another implementation, the composition is in the form of a transdermal cream that is applied on a dermal surface of the individual.

In at least some implementations of the present invention, the dietary supplement or composition provided estrogenic effects in the body, but the dietary supplement or composition is milder than estrogen and therefore does not have the accompanying side effects. For example, hormone replacement therapy can induce cancer in estrogen dependent cells in such areas of the body as the breast, the uterus and/or the ovaries, the utilization of the dietary supplement is preferred because the excretion is slower.

The dietary supplement or composition provides the ability to substitute these to act as a substitute in the hormone replacement therapy and they are weaker and so if you have high concentrations of natural estrogen then they weaken the activity of the natural estrogen and if there are very low concentrations of natural estrogen, then they support the estrogenic action.

In some implementations, the women receive the extract of the leaves, the juice, or another product of the *Morinda citrifolia* in the form of a liquid, a dry capsule or as a cream. In one implementation, the individual consumes at least a gram a day. Accordingly, in accordance with at least some implementations of the present invention, a dietary supplement is provided that is consumed or otherwise used by an individual to provide estrogenic effects within the individual's body to prevent or overcome such symptoms as hot flashes, night sweating, bleeding, depression, such as at the onset of menopause. The dietary supplement further prevents or improves osteoporosis.

There are two types of cells which are responsible called osteoblasts and osteoclasts. The osteoblast cells are for remodeling of the bone and the osteoclast cells are for these saluting of bone material. The calcium level of the blast is to be on a constant level and the bone is a buffer for the calcium level. If the calcium level is decreased in the blood then bone material will be saluted in giving and raising the calcium level. And if a woman is pregnant the embryo takes a lot of calcium extract from the blood because it has to build it's own skeleton. And, therefore the turnover of bone material in the mother's skeleton is to be increased. There is a high level of estrogen during pregnancy and the estrogen is important for this process in these osteoblast cells, which are important for remodeling of bones and during menopause the estrogen level is going down. The remodeling process becomes weaker and women lose bone material and get osteoporosis. So, this is a way of providing estrogenic effects to help replenish the body. Accordingly, in accordance with at least some implementations of the present invention, a processed product from the *Morinda citrifolia*, such as from the leaves, the juice or another part of the *Morinda citrifolia*, is used to selectively provide estrogenic effects in the body.

In at least some implementations, the dietary supplement further inhibits aromatase or aromatase enzymes that function to convert androgens to estrogens, thereby inhibiting receptors from binding with estrogen, and reducing and/or regulating estrogen production as well as reducing the amount of estrogen produced within the body and regulating such production through the inhibition of aromatase, for the treatment of cancer, and particularly for the treatment of estrogen-dependent cancerous tumors, through the introduction into the body (e.g. ingesting) a safe, pre-determined dosage of a naturaceutical composition formulated with or comprising one or more processed *Morinda citrifolia* products for a safe, pre-determined duration.

In one implementation, a quantity of a processed *Morinda citrifolia* product is obtained in the form of fruit juice, leaves, puree juice or juice puree, pulp, seed oil, and/or dietary fiber, using the process(es) as described herein. Subsequently, an amount of any one of or a combination of these is formulated with other ingredients to create a naturaceutical composition formulated to provide significant health advantages and to assist in the treatment of and provide preventative effects upon cancerous cells through the inhibition of aromatase enzymes.

Implementation of the present invention features a naturaceutical composition formulated with at least one processed *Morinda citrifolia* product for the inhibition of aromatase or aromatase enzymes within the body of a mammal; and a method of administering the same.

Implementation of the present invention further embraces a naturaceutical composition that comprises at least one processed *Morinda citrifolia* product in one of its several forms (preferably the fruit juice or powder from the leaves), formulated with other ingredients, either natural or artificial, as needed. The preferred naturaceutical composition is a liquid that may be administered orally or through intravenous injection, wherein the active ingredients, namely *Morinda citrifolia*, are allowed to be absorbed into the tissues to inhibit aromatase and reduce/regulate estrogen production.

Implementation of the present invention further features a method of inhibiting aromatase and treating, inhibiting, preventing, and reversing cancer cell growth through the prophylactic administration of a naturaceutical composition comprising at least one processed *Morinda citrifolia* product as an active ingredient.

While the methods and processes of the present invention have proven to be particularly useful in the area of selectively inhibiting estrogen production and/or providing estrogenic effects in the body, those skilled in the art can appreciate that the methods and processes can be used in a variety of different applications, and in a variety of different forms, to yield a composition that includes a processed product from the *Morinda citrifolia* to provide selective estrogenic control by inhibiting estrogen production and/or providing a mild estrogenic effects.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

There is evidence that women eating a diet rich in phytoestrogens have less problems with menopause.

The estrogenic activity of an alcoholic leaf extract of *Morinda citrifolia* was investigated using two in vitro assays. (1.) Estrogen replacement on isolated estrogen receptor alpha and -beta (ER-alpha, ER-beta); and (2.) Induction of Alkaline phospaphatase in Isikawa cells (human endometrium carcinoma). An alcoholic extract of pulverized dry leafs of *Morinda citrofolia* (origin Tahiti) was used. One ml of the extract represented 100 ml of leafs.

Regarding estrogen replacement, recombinant ER-alpha and ER-beta were purchased. The receptors were saturated with tritium labelled estradiol. After addition of the test substance the free unbound radioactivity is measured. The method used was in accordance with Kuiper et al., 1998. Kuiper G G, Lemmen J G, Carlsson B, Corton J C, Safe S H, van der Saag P T, van der B B and Gustafsson J A (1998) Interaction of Estrogenic Chemicals and Phytoestrogens with Estrogen Receptor Beta. *Endocrinology* 139: pp 4252-4263.

Figure 1:
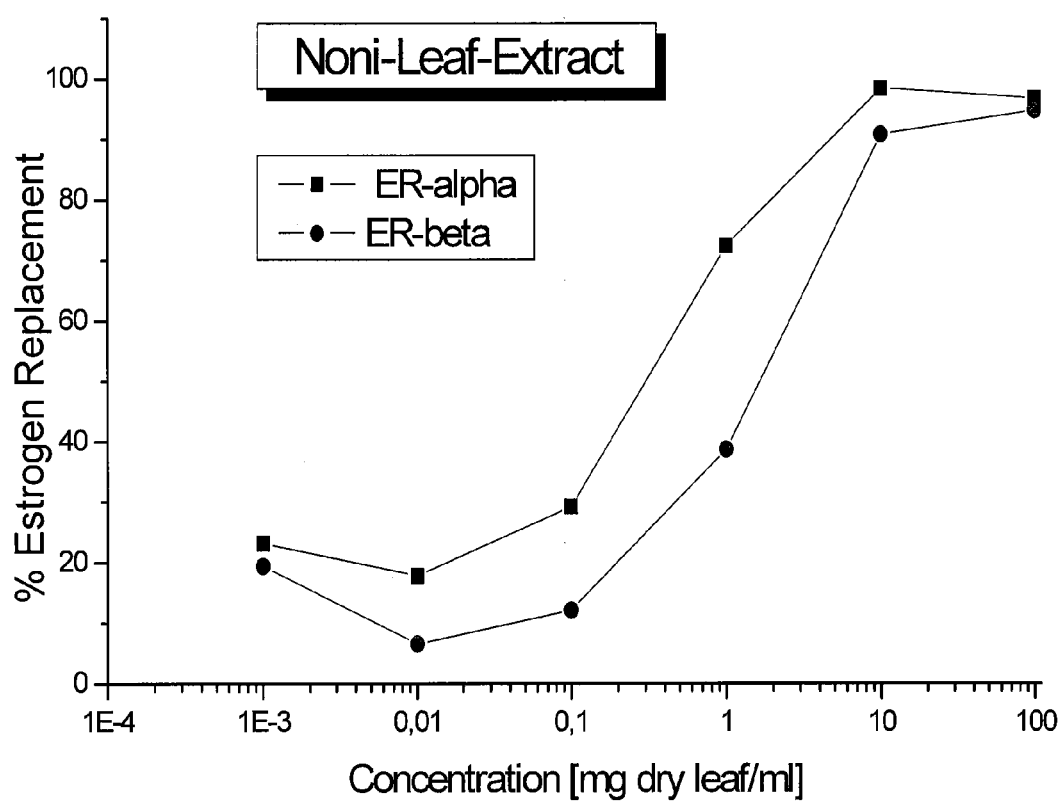
FIG. 1 illustrates estrogen replacement at various concentrations of leaf extract.

The results as shown in FIG. 1, indicated that a strong replacement of estradiol from both receptors was observed. The replacement reached the 100% level, which is remarkable for phytoestrogens. The affinity of the leaf extract to ER-alpha was almost 5-times greater than to ER-beta.

The induction of the enzyme alkaline phosphatase is under control of the estrogen receptor. It is known that estradiol has a regulating function on bone remodelling. Alkaline phosphatase is the key enzyme for this process. Ishikawa cells are used as a model to investigate the agonistic action of compounds with estrogenic acivity (Wober J, Weisswange and Vollmer G (2002) Stimulation of Alkaline Phosphatase Activity in Ishikawa Cells Induced by Various Phytoestrogens and Synthetic Estrogens. *J Steroid Biochem Mol Biol* 83: pp 227-233).

Figure 2:
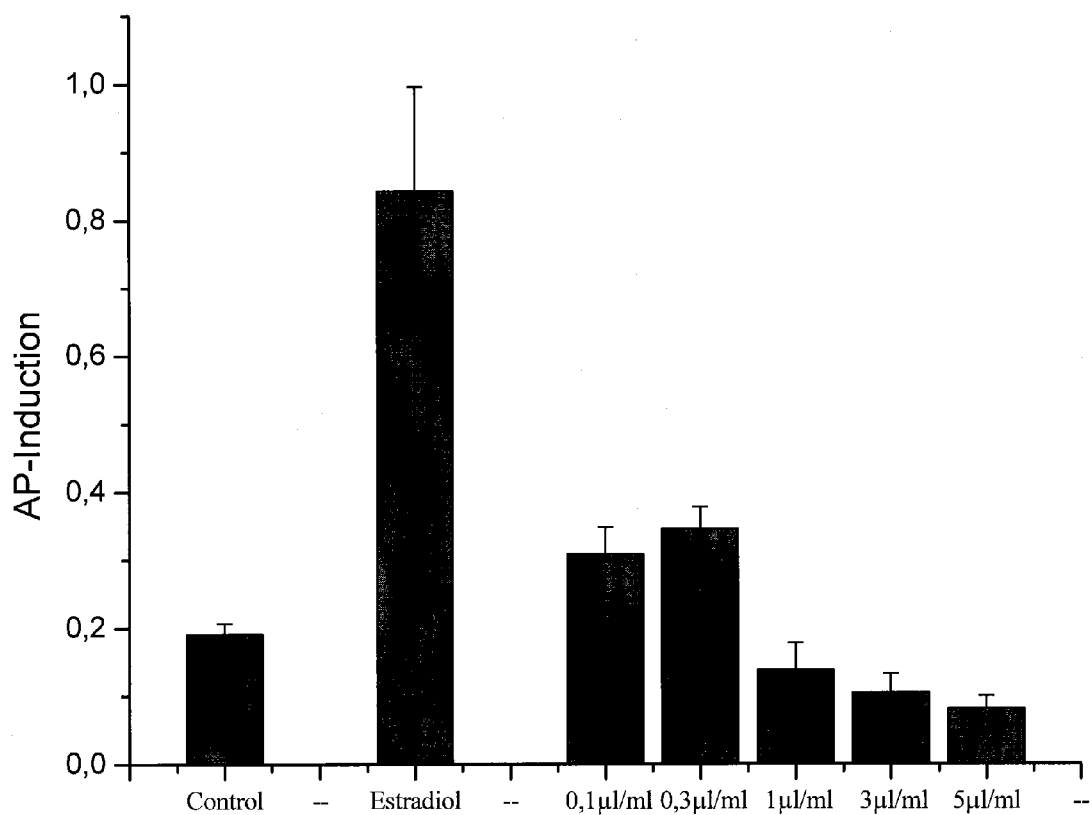
FIG. 2 illustrates AP-induction effects of leaf extract.

As shown in FIG. 2, the *Morinda citrifolia*-leaf-extract exerted a moderate but significant induction of alkaline phosphatase in Ishikawa cells. The maximum effect was achieved at 0.3 ml/ml (representing 30 mg dry leafs/ml). Higher concentrations caused an inhibition of the enzyme induction.

Accordingly, the estrogenic activity of an alcoholic extract of the leaves of *Morinda citrifolia* was demonstrated in two in vitro assays, commonly used for the investigation of estrogenic activity. Both assays showed positive effects. The results suggest a potential use of Noni leafs for the treatment of symptoms caused by a lack of estrogen (e.g. menopause, ovariectomy).

Phytoestrogens and estrogen-like molecules are able to bind to estrogen receptors, which in turn mimic estrogenic activities in cells and tissues. Recently, the isoflavones from soy plants have demonstrated selectivity pertaining to selective estrogen receptor modulators (SERMs) with health benefits that have no adverse effects. The benefits may include prevention of breast cancer and can cause growth arrest and in some cases, the apoptosis in prostrate cancer cells in-vitro and in-vivo and also osteoporosis.

Some of the phytoestrogens have been reported to possess anti-androgenic effects and anti-oxidant activities. The mechanisms include the inhibition of $5\alpha$-reductase, $17\beta$-hydroxysteroid dehydrogenase, aromatase, tyrosine specific protein kinases and DNA topoisomerase II. One of the best explanations offered for the biological activity of estrogen-like molecules concluded that phytoestrogens are weakly estrogenic but induce some distinct patterns of ER agonist and ER antagonist activities that are cell context- and promoter-dependant, suggesting that these weakly estrogenic compounds will induce tissue-specific in vivo ER agonist or antagonist activities.

DETAILED DESCRIPTION OF THE INVENTION

The present invention relates to estrogenic effects in the human body. More particularly, the present invention relates to the utilization of a dietary composition or supplement to selectively inhibit estrogen production and to provide estrogenic effects in the human body, wherein the composition is formulated with one or more processed products from the Indian Mulberry plant, scientifically known as *Morinda citrifolia L.*

The present invention describes and features a method and formulation for selectively inhibiting estrogen production and to provide estrogenic effects, and for treating and preventing cancerous cell growth within a mammal, as well as for reducing estrogen production in mammals that contributes to the growth of estrogen-dependent cancerous tumors, each through the prophylactic administration of a naturaceutical formulation comprising at least one *Morinda citrifolia* product in processed form.

The presently preferred embodiments of the invention will be best understood, and its benefits and advantages more clearly pointed out, by separating the following more detailed description into sections, the first pertaining to a general discussion regarding *Morinda citrifolia*, including its origins, processing techniques, and health benefits, as well as the methods employed to produce and manufacture the processed *Morinda citrifolia* products used as key active ingredients in the naturaceutical formulations described herein, the second being a more detailed and specific discussion relating to formulations and compositions comprising the processed *Morinda citrifolia* product used to provide estrogenic effects, and the third being a more detailed and specific discussion relating to naturaceutical formulations and compositions comprising the processed *Morinda citrifolia* product used to inhibit aromatase and reduce/regulate estrogen production within the body, as well as the various methods for administering these naturaceuticals to inhibit the growth, proliferation, metastasizing, and vitality of estrogen-dependent cancerous cells. Examples of experimental studies and the results obtained are also provided herein.

Accordingly, the following disclosure of the present invention is grouped into three subheadings, namely "Dietary Supplement," "Providing Estrogenic Effects," and "Inhibiting Estrogen Production." The utilization of the subheadings is for convenience of the reader only and is not to be construed as limiting in any sense.

Dietary Supplement

Embodiments of the present invention take place in association with a dietary supplement that is processed from a product of the Indian Mulberry plant, scientifically known as *Morinda citrifolia* L. ("*Morinda citrifolia*"), which is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below.

Because the *Morinda citrifolia* fruit is for all practical purposes inedible, the fruit must be processed in order to make it palatable for human consumption and included in the naturaceutical used to provide estrogenic effect, to inhibit aromatase, and to treat various cancer cells. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other process include freeze drying the fruit and juice. The fruit and juice can be reconstituted during production of the final juice product. Still other processes include air drying the fruit and juices, prior to being masticated.

Embodiments of the present invention contemplate extraction of a *Morinda Citrifolia* product from the leaves of the *Morinda Citrifolia* and using the product in a composition for use in a capsule or tablet for consumption to inhibit estrogen production and provide estrogenic effects in a body.

Embodiments of the present invention also contemplate the use of fruit juice and/or puree fruit juice extracted from the *Morinda Citrifolia* plant. In a currently preferred process of producing *Morinda citrifolia* fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions.

The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

Each product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181° F. (83° C.) minimum and then packed in drums for further processing or made into a high fiber product.

The processed *Morinda citrifolia* product may also exist as a dietary fiber. Further, the *Morinda Citrifolia* product may exist as an extract (e.g., powdered extract) taken from the leaves of the *Morinda Citrifolia*. Still further, the processed *Morinda citrifolia* product may also exist in oil form. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* is rich in natural ingredients. For example, the natural ingredients include: (from the leaves) alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; (from the flowers) acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta rhamnosyl-glucopyranoside; (from the fruit) acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; (from the roots) anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; (from the root bark) alizarin, chlororubin, glycosides (pentose, hexose), morindadiol, morindanigrine, morindine, morindone, resinous matter, rubiadin monomethyl ether, and soranjidiol; (from the wood) anthragallol-2,3-dimethylether; (from the tissue culture) damnacanthal, lucidin, lucidin-3-primeveroside, and morindone-6beta-primeveroside; and (from the plant) alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy. Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer. Third, Xeronine assists in enlarging the membrane pores of the cells. This enlargement allows for larger chains of peptides (amino acids or proteins) to be admitted into the cell. If these chains are not used they become waste. Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothaches, blemishes, immune system failure, and others.

The compositions containing *Morinda citrifolia* may be in a form suitable for oral use, systemic administration, injection, and others. In regards to an oral composition, such a composition may exist, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

Thus, embodiments of the invention selectively inhibit estrogen production and provide estrongenic effects. In some embodiments, a liquid or dry extract comprises the product from the *Morinda citrifolia*. In a further embodiment, the produce is provided in capsules to facilitate consumption. In some embodiments, at least one gram is consumed daily for as long as is needed for treating the symptoms.

Providing Estrogenic Effects

As provided above, the present invention relates to controlling estrogenic effects in the human body. More particularly, the present invention relates to the utilization of a dietary composition or supplement to selectively inhibit estrogen production and to provide an estrogenic effect in the human body, wherein the composition is formulated with one or more processed products from the Indian Mulberry plant, scientifically known as *Morinda citrifolia* L.

Phytoestrogens are certain compounds occurring in plants, which mimic the action of natural estrogens. Among plants rich in phytoestrogens are: black cohosh (*Cimicifuga racemosa*), soy (*Glycine max*.), red clover (*Trifolium pratense*) and hops (*humulus lupulus*) Our data show that *Morinda citrifolia* (fruits and leafs) does also contain estrogenic activity. There is evidence that women eating a diet rich in phytoestrogens have less problems with menopause.

The estrogenic activity of an alcoholic leaf extract of *Morinda citrifolia* was investigated using two in vitro assays. (1.) Estrogen replacement on isolated estrogen receptor alpha and -beta (ER-alpha, ER-beta); and (2.) Induction of Alkaline phospaphatase in Isikawa cells (human endometrium carcinoma). An alcoholic extract of pulverized dry leafs of *Morinda citrofolia* (origin Tahiti) was used. One ml of the extract represented 100 µl of leafs.

Regarding estrogen replacement, recombinant ER-alpha and ER-beta were purchased. The receptors were saturated with tritium labelled estradiol. After addition of the test substance the free unbound radioactivity is measured. The method used was in accordance with Kuiper et al., 1998. Kuiper G G, Lemmen J G, Carlsson B, Corton J C, Safe S H, van der Saag P T, van der B B and Gustafsson J A (1998) Interaction of Estrogenic Chemicals and Phytoestrogens with Estrogen Receptor Beta. Endocrinology 139: pp 4252-4263.

The results indicated that a strong replacement of estradiol from both receptors was observed. The replacement reached the 100% level, which is remarkable for phytoestrogens. The affinity of the leaf extract to ER-alpha was almost 5-times greater than to ER-beta.

The induction of the enzyme alkaline phosphatase is under control of the estrogen receptor. It is known that estradiol has a regulating function on bone remodelling. Alkaline phosphatase is the key enzyme for this process. Ishikawa cells are used as a model to investigate the agonistic action of compounds with estrogenic acivity (Wober J, Weisswange I and Volimer G (2002) Stimulation of Alkaline Phosphatase Activity in Ishikawa Cells Induced by Various Phytoestrogens and Synthetic Estrogens. J Steroid Biochem Mol Biol 83: pp 227-233).

As shown in FIG. 2, the *Morinda citrfolia*-leaf-extract exerted a moderate but significant induction of alkaline phosphatase in Ishikawa cells. The maximum effect was achieved at 0.3 ml/ml (representing 30 mg dry leafs/ml). Higher concentrations caused an inhibition of the enzyme induction.

Accordingly, the estrogenic activity of an alcoholic extract of the leaves of *Morinda citrfolia* was demonstrated in two in vitro assays, commonly used for the investigation of estrogenic activity. Both assays showed positive effects. The results suggest a potential use of Noni leafs for the treatment of symptoms caused by a lack of estrogen (e.g. menopause, ovariectomy).

Phytoestrogens and estrogen-like molecules are able to bind to estrogen receptors, which in turn mimic estrogenic activities in cells and tissues. Recently, the isoflavones from soy plants have demonstrated selectivity pertaining to selective estrogen receptor modulators (SERMs) with health benefits that have no adverse effects. The benefits may include prevention of breast cancer and can cause growth arrest and in some cases, the apoptosis in prostrate cancer cells in-vitro and in-vivo and also osteoporosis.

Some of the phytoestrogens have been reported to possess anti-androgenic effects and anti-oxidant activities. The mechanisms include the inhibition of $5\alpha$-reductase, $17\beta$-hydroxysteroid dehydrogenase, aromatase, tyrosine specific protein kinases and DNA topoisomerase II. One of the best explanations offered for the biological activity of estrogen-like molecules concluded that phytoestrogens are weakly estrogenic but induce some distinct patterns of ER agonist and ER antagonist activities that are cell context- and promoter-dependant, suggesting that these weakly estrogenic compounds will induce tissue-specific in vivo ER agonist or antagonist activities.

The induction of the enzyme alkaline phosphatase is under control of the estrogen receptor. It is known that estradiol has a regulating function on bone remodelling. Alkaline phosphatase is the key enzyme for this process. Ishikawa cells are used as a model to investigate the agonistic action of compounds with estrogenic activity (Wober J, Weisswange I and Vollmer G (2002) Stimulation of Alkaline Phosphatase Activity in Ishikawa Cells Induced by Various Phytoestrogens and Synthetic Estrogens. *J Steroid Biochem Mol Biol* 83: pp 227-233).

The *Morinda citrifolia*-leaf-extract exerted a moderate but significant induction of alkaline phosphatase in Ishikawa cells. The maximum effect was achieved at 0.3 ml/ml (representing 30 mg dry leafs/ml). Higher concentrations caused an inhibition of the enzyme induction.

Accordingly, the estrogenic activity of an alcoholic extract of the leaves of *Morinda citrifolia* was demonstrated in two in vitro assays, commonly used for the investigation of estrogenic activity. Both assays showed positive effects. The results suggest a potential use of Noni leafs for the treatment of symptoms caused by a lack of estrogen (e.g. menopause, ovariectomy).

Phytoestrogens and estrogen-like molecules are able to bind to estrogen receptors, which in turn mimic estrogenic activities in cells and tissues. Recently, the isoflavones from soy plants have demonstrated selectivity pertaining to selective estrogen receptor modulators (SERMs) with health benefits that have no adverse effects. The benefits may include prevention of breast cancer and can cause growth arrest and in some cases, the apoptosis in prostrate cancer cells in-vitro and in-vivo and also osteoporosis.

Some of the phytoestrogens have been reported to possess anti-androgenic effects and anti-oxidant activities. The mechanisms include the inhibition of 5α-reductase, 17β-hydroxysteroid dehydrogenase, aromatase, tyrosine specific protein kinases and DNA topoisomerase II. One of the best explanations offered for the biological activity of estrogen-like molecules concluded that phytoestrogens are weakly estrogenic but induce some distinct patterns of ER agonist and ER antagonist activities that are cell context- and promoter-dependant, suggesting that these weakly estrogenic compounds will induce tissue-specific in vivo ER agonist or antagonist activities.

Several studies have proven that certain phytoestrogens can inhibit the enzymes that convert the androgens to estrogens namely aromatase and 17β-hydroxsteroid dehydrogenase type 1 & 5 but not the others. As provided below, a dietary supplement having a processed product of *Morinda citrifolia* inhibits aromatase enzyme. Such a dietary supplement also provides estrogenic effects.

Tahitian Noni® Juice has a higher antioxidant property than pycnogenol. Compounds that work like estrogen but without the side effects have been found to prevent brittle bone disease in mice. That discovery may offer some help and relief that is much need for older women who stopped using hormone replacement therapy (HRT) because of the risks of cancer and heart diseases that are associated with HRT.

In the past hormone replacement therapy (HRT) with estrogen and estrogen derivatives was used as a prophylaxis against the osteoporosis and in some countries it is not allowed anymore because of the side effects. So, the hormone replacement therapy is restricted for severe symptoms, but women like to treat their mild symptoms also because they don't like it.

Tahitian Noni® Puree Juice Concentrate (TNPJC) dry form was evaluated for possible estrogenic agonism is ICT derived immature female mice at a maximum tolerated dose of 4000 mg/kg administered orally once daily for 3 consecutive days. The dry form of TNPJC resulted from using a Rotor Vap with pressure and low temperature.

It was found that the dose of 4000 mg/kg administered causes an increase of the uterine wet weight (not dry weight) by about 50% relative to the vehicle group (β-Estadiol 3-Benzoate at 0.03 ma/kg causes an 83% increase in uterine wet weight) which indicates a possible estrogen agonist activity. This may also suggest a dose dependant manner.

A huge dose of dry form of TNPJC causes a 50% increase while a minute dose (0.03 mg/kg) of Estradiol 3-Bensoate causes a dramatic increase in the weight gain observed above).

Briefly, the anti-aromatase effects of Tahitian Noni-Puree Juice Concentrate, anticancer, antioxidant and other beneficial effects of Tahitian Noni prevents the side effects of estrogen like compounds but also has estrogenic like effects at the design dose which may explain the benefits for peri- and postmenopausal women such as preventing osteoarthritis, osteoporosis and other health benefits already mentioned above.

In accordance with embodiments of the present invention, the dietary supplement having a processed product of *Morinda citrifolia* provides mild estrogenic effects. Natural hormones have very fast turnover so they are discharged by insomatic processes and so if in order to guarantee a fast regulating system you have to get control of the regulator which is the hormone, the only way is to remove it in order to allow new hormone to be released by the system. So, if you take the natural estrogen, the half life of this component is very short. So, in order to provide a constant level of hormone you have take a compound which is active like the natural hormone does but is not removed so fast from the system and therefore some chemical variations are made on the molecule.

For example, the steroidal contains 1 estrogen group on this system and the natural enzymes which remove the estrogen from the blood cannot convert the derivative—it remains active for a longer time in the body. For a constant treatment over days or weeks you cannot use a natural hormone you have to take the derivatives which are removed more slowly from the body. Accordingly, the dietary supplement with the processed *Morinda citrifolia* product may be used. It acts very similar to the natural hormone and is very strong. The action is very strong and sometimes more than the natural hormone, and therefore the side effects of the hormone are enhanced by these compounds. And the phytolestrogens are no estrogens from a chemical standpoint but from a biological standpoint they are. So because they act to provide estrogenic effects, they interfere with the system and the reaction or the outcome is similar but not the same like that of estrogen. The action is weaker—it does not have the peaks of action.

In the presence of estrogen they can also antagonize the estrogenic action. So there is a lot of discussion momentarily about the suitably of the vital estrogens. Women eating a diet rich in phytolestrogens have lower incidences of breast cancer and less problems with menopause so phytolestrogens are in a variety of natural foods—especially soy and other plants. Soy is rich in phytolestrogens and the women in Japan and China eat a lot of soy products.

In accordance with at least some embodiments of the present invention, the dietary supplement having the processed *Morinda citrifolia* product may be provided in capsules or in a cream, such as a transdermal or transmucosal cream.

The absorbtion rate for the processed *Morinda citrifolia* leaves is high for the ingesting. In order to find an estrogenic active compound you have to have a certain endpoint. So what the estrogen does in the body or cells is that it finds a receptor which was in the cell and then it binds to the receptor and then this complex of estrogen and receptor binds to the DNA and then initiates the induction of certain proteins which are then produced by the cells and so that's a mechanism of action. So, therefore you can follow this mechanism in order to find an estrogenic activity.

First you show that the compound binds to the receptor in order to do that you take the receptor saturate it with the natural estrogen in the radioactive form and when you then add another compound to the receptor then this compound will release the estrogen from the receptor because there is a competition between the natural estrogen and the other estrogen the competition at the receptor site. If the compound binds it releases estrogen. You can tell that it binds, which is the first step, but it does not tell you whether it will do the next step—the estrogen receptor complex binds to the DNA and initiates the induction of the percentages of certain proteins.

The compound can bind to the estrogen receptor but then not in use of the estrogenic action then if it does this then it acts as an antagonist. Then it inhibits the action of the estrogen because it occupies the receptor so that estrogen does not find a free receptor and then it cannot act. And so but we are looking for compounds which bind to the receptor and then act as an estrogen. It induces the services of certain proteins. So therefore we do both assays. At first we investigate the binding to the receptor and secondly we look for an action end point.

The extract from the leaves of the morinda citrifolia reacts like estrogen to provide estrogenic effects. However, it acts weaker than the natural estrogen and thus does not have the side effects.

If during hormone replacement therapy the disadvantage is that it can induce cancer in estrogen dependent cells like breast, uterus, ovaries so if you treat with high doses of estrogen or what they take are synthetic estrogens which are derived from the natural estrogen but the action lasts longer because excretion is slower. If you treat women over a certain period maybe years with high doses of the estrogens then the incidences of breast cancer or uterus cancer of cancer of the ovaries increases especially breast cancer and endometrial cancer.

And so therefore we try to get to refuse the hormone replacement therapy but, women need another substitute in the hormone replacement therapy and they are weaker and so the interesting thing with these compounds is that if you have high concentrations of natural estrogen then they act like antagonists, which means they weaken the activity of the natural estrogen and if there are very low concentrations of natural estrogen, then they act as estrogens so they support the estrogenic action or have estrogenic effects. So that means that the extremes that they help women to not experience extreme situations of high estrogen concentration or very low estrogen concentration.

Symptoms that women typically experience includes hot flashes, night sweating and/or depression at the onset of the menopause sometimes before the bleeding stops permanently. They have very strong bleeding and depression. Another long term effect is osteoporosis so the bone material is permanent change in bone material so that means they bone material is so loose and it solidifies again. So there are two types of cells which are responsible called osteoblasts and osteoclasts. The osteoblast cells are for remodeling of the bone and the osteoclast cells are for these saluting of bone material so this is important because the calcium level of the blast is to be on a constant level and the bone is a buffer for the calcium level. If the calcium level is decreased in the blood then bone material will be saluted in giving and rising the calcium level. And if a women is pregnant the embryo takes a lot of calcium extracts from the blood because it has to rebuild it's own bone skeleton. And therefore the turnover of bone material in the mothers skeleton has to be increased and the estrogen during pregnancy, there is a high level of estrogen and the estrogen is important for this process in these osteoblast cells which are important for remodeling of bones and during menopause the estrogen level is going down and then the remodeling process becomes weaker and then women lose bone material and get osteoporosis.

An elvaluation was performed in Enzyme and Radioligand Binding assays, of the activity of compound MDA-6 (PT#1026431). Methods employed in this study have been adapted from the scientific literature to maximize reliability and reproducibility. Reference standards were run as an integral part of each assay to ensure the validity of the results obtained. Assays were performed under conditions described in the accompanying "Methods" section of this report. The literature reference(s) for each assay are in the "Literature References" section. If either of these sections were not originally requested with the accompanying report, please contact us at the number below for a printout of either of these report sections.

Where presented, $IC_{50}$ values were determined by a non-linear, least squares regression analysis using Data Analysis ToolboX™ (MDL Information Systems, San Leandro, Calif., USA). Where inhibition constants ($K_i$) are presented, the $K_i$ values were calculated using the equation of Cheng and Prusoff (Cheng, Y., Prusoff, W. H., Biochem. Pharmacol. 22:3099-3108, 1973) using the observed $IC_{50}$ of the tested compound, the concentration of radioligand employed in the assay, and the historical values for the $K_d$ of the ligand (obtained experimentally at MDS Pharma Services). Where presented, the Hill coefficient ($n_H$), defining the slope of the competitive binding curve, was calculated using Data Analysis ToolboX™. Hill coefficients significantly different than 1.0, may suggest that the binding displacement does not follow the laws of mass action with a single binding site. Where $IC_{50}$, $K_i$, and/or $n_H$ data are presented without Standard Error of the Mean (SEM), data are insufficient to be quantitative, and the values presented ($IC_{50}$, $K_i$, $n_H$) should be interpreted with caution.

A summary of the results provided the following table(s) in rank order of potency for estimated $IC_{50}$ and/or $K_i$ values. Biochemical assay results are presented as the percent inhibition of specific binding or activity throughout the report. All other results are expressed in terms of that assay's quantitation method. For primary assays, only the lowed concentration with a significant response judged by the assays' criteria, is shown in this summary. Where applicable, either the secondary assay results with the lowest dose/concentration meeting the significance criteria or, if inactive, the highest dose/concentration that did not meet the significance criteria is shown. Unless otherwise requested, primary screening in duplicate with quantitative data (e.g., IC50±SEM, Ki±SEM and nH) are shown where applicable for individual requested assays. In screening packages, primary screening in duplicate with semi-quantitative data (e.g., estimated IC50, Ki and nH) are shown where applicable (concentration range of 4 log units); available secondary functional assays are carried out (30 μM) and MEC or MIC determined only if active in primary assays >50% at 1 log unit below initial test concentration. Significant response (≧50% inhibition or stimulation for Biochemical assays) were noted in the primary assays listed below:

| | | | | | | | |
|---|---|---|---|---|---|---|---|
| | PRIMARY TESTS | | | | | | |
| CAT. # | Primary Biochemical Assay | Species | Conc. | % Inh. | $IC_{50}$* | $K_i$ | $n_H$ |
| 136010 | Lipoxygenase 5-LO | hum | 1% | 103 | | | |
| 226010 | Estrogen ER | hum | 1% | 99 | 0.31% | 0.09% | 3.7 |
| 226050 | Estrogen ERβ | hum | 1% | 99 | .028% | 0.06% | 3.28 |

-continued

ABOVE PRIMARY TESTS IN RANK ORDER OF POTENCY

| CAT. # | Primary Radioligand Assay | Species | Conc. | % Inh. | IC$_{50}$* | K$_i$ | n$_H$ |
|---|---|---|---|---|---|---|---|
| 226050 | Estrogen ERβ | hum | 1% | 99 | 0.28% | 0.06% | 3.28 |
| 226010 | Estrogen ER | hum | 1% | 99 | 0.31% | 0.09% | 3.7 |

*A standard error of the mean is presented where results are based on multiple, independent determinations.
gp = guinea pig;
hum = human
*Batch: Represents compounds tested concurrently in the same assay(s).
♦Denotes item meeting criteria for significance
$^f$Results with ≧50% stimulation or inhibition are boldfaced. (Negative values correspond to stimulation of binding or enzyme activity)
$^R$= Additional Comments 136010 Lipozygenase 5-LO
Source: Human PBMN cells
Substrate: Endogenous arachidonic acid from PBMNC
Vehicle: 100% H$_2$O
Pre-Incubation Time/Temp: 15 minutes @37° C.
Incubation Time/Temp: 15 minutes @37° C.
Incubation Buffer: HBSS (Hank's Balanced Salt Solution)
Quantitation Method: EIA quantitation of LTB$_4$
Significance Criteria: ≧50% of max stimulation or inhibition
226010 Estrogen ER
Source: Human recombinant insect Sf9 cells
Ligand: 0.5 nM $^3$H Estradiol
Vehicle: 100% H$_2$O
Incubation Time/Temp: 2 hours @25° C.
Incubation Bugger: 10 mM Tris-HCl, pH 7.5, 10% Glycerol, 1 mM DTT, 1 mg/ml BSA
NonSpecific Ligang: 1 μM Diethylstilbestrol
K$_d$: 0.2 nM*
B$_{max}$: 1400 pmole/mg Protein*
Specific Binding: 85%*
Quantitation method: Radioligand Binding
Significance Criteria: ≧50% of max stimulation or inhibition
250600 Leukotriene D 4
Source: Duncan Hartley derived Guinea pig lung
Ligand: 0.2 nM $^3$H Leukotriene D$_4$ (LTD$_4$)
Vehicle: 100% H$_2$O
Incubation Time/Temp: 60 minutes @25° C.
Incubation Buffer: 50 mM Tris-HCl, 0.01% BSA, 5 mM CaCl$_2$, 5 mM MgCl$_2$, 100 μg/mL Bacitracin, 1 mM Phenylmethylsulfonyl Fluoride
NonSpecific Ligand: 0.1 μM Leukotriene D$_4$ (LTD$_4$)
K$_d$: 0.2 nM*
B$_{max}$: 0.24 pmole/mg Protein*
Specific Binding: 85%*
Quantitation method: Radioligand Binding
Significance Criteria: ≧50% of max stimulation or inhibition
226050 Estropen ERβ
Source: Human recombinant insect Sf9 cells
Ligand: 0.5 nM $^3$H Estradiol
Vehicle: 100% H$_2$O
Incubation Time/Temp: 2 hours @25° C.
Incubation Buffer: 10 mM Tris-HCl, pH 7.5, 10% Glycerol, 1 mM DTT, 1 mg/ml BSA
NonSpecific Ligand: 1 μM Diethyistilbestrol
K$_d$: 0.13 nM*
B$_{max}$: 3000 pmole/mg Protein*
Specific Binding: 90%*
Quantitation method: Radioligand Binding
Significance Criteria: ≧50% of max stimulation or inhibition
271200 Serotonin 5-HT$_{1B}$
Source: Wistar Rat cerebral cortex
Ligand: 10 pM $^{125}$I CYP
Vehicle: 100% H$_2$O
Incubation Time/Temp: 90 minutes @37° C.
Incubation Buffer: 50 mM Tris-HCl, 154 mM NaCl, 10 μM Pargyline, 30 μM Isoprenaline, pH 7.7
NonSpecific Ligand: 10 μM Serotonin (5-HT)
K$_d$: 0.19 nM*
B$_{max}$: 0.142 pmole/mg Protein*
Specific Binding: 70%*
Quantitation method: Radioligand Binding
Significance Criteria: ≧50% of max stimulation or inhibition Accordingly, the estrogen receptors displayed a higher capacity for biding NSAID ligands with greater affinity. Many of these ligands, mix agonist and antagonist, have been developed and are used in the treatment of postmenopausal women. Moreover, steroidal estrogens not only play an important role in the growth of the organisms but also in the differentiation of certain cells, function of male and female reproductive systems, the positive effects on osteoblast and its activities, the cardiovascular and the central nervous systems.

The effects described above are mediated by two intranucleoproteins such as ERα and ERβ. The binding of estrogens or estrogen like molecules to these intranuceloproteins leads to structural conformational changes, which in turn dimerizes the ligand-receptor complex, later leads to activation of genes under their control at the DNA.

It has been documented that xenoestrogens, phytoestrogens and synthetic estrogens are able to bind to these estrogen receptors, which in turn mimic the activities of the human estrogen in a particular cell and tissues in a specific manner such as those that are well known in the reproductive systems. However, estrogen and estrogen like molecules and its receptors may act in various regions through out the body and in particular the brain. Estrogen and estrogen like molecules act as powerful neuroprotective antioxidant, which may activate transcription of genes for neuroprotection directly or indirectly.

Any compounds that act through these nucleoprotein receptors can have either a stimulating effect (agonist) on certain tissues (such as bone tissue and antagonist in others) and a blocking effect (antagonist) in other tissues (in the case of breast and uterus cancer). Some recent scientific studies suggest that the ERα form is more important than the ERβ in regulating the cardiac rhythm and frequencies. Therefore several suggestions has been made regarding selective antagonist ERα in order to effectively control heart activities.

Experimentation was performed to evaluate activity of Tahitian Noni® Puree Juice Concentrate in a Radioligand Binding Assay to indicate the effects of Tahitian Noni® Puree Juice Concentrate & Tahitian Noni® Juice on Estrogen Receptors ERα and ERβ, and the following were the results:
    1% Tahitian Noni Puree Juice Concentrate=99% Inhibition of ERα with IC$_{50}$ 0.31%
    1% Tahitian Noni Puree Juice Concentrate=99% Inhibition of ERβ with IC$_{50}$ 0.28%

2% Tahitian Noni® Juice=20% Inhibition of ERα
2% Tahitian Noni® Juice=40% Inhibition of ERβ

These results seems to suggest that there is a dose dependant effect of Tahitian Noni® Juice on the inhibition of the estrogen receptors ERα and ERβ respectively compared to Tahitian Noni Puree Juice Concentrate in these in-vitro studies. Furthermore, these results suggest that Tahitian Noni® Juice and Tahitian Noni Puree Juice Concentrate are beneficial for cardio-protection, treatment of postmenopausal symptoms, osteoarthrithis, breast cancer, uterine cancer and colon cancer.

The following discusses estrogen agonist activity of processed *Morinda citrifolia* products. What that means is estrogen is a hormone with many properties so hormones are needed to balance your internal system. So in order to bond this you have a nervous system and the hormonal system and estrogen especially is used to make the body to proliferate which means to give birth to babies and it helps it on every stage that means the very first one is to force them to get attracted to men so estrogens help her to grow and makes the skin weak and things which men like on women and within the body it regulates different cells which so every organ is special it's a special role in this proliferation process so the uterus for example at the time when the conception takes place the uterus has to susceptible to harvest the egg and then to nourish it and then when they embryo grows new blood vessels have to grow out of the uterine and penetrate the embryo in order to feed it so therefore the estrogen can induce this outgrowth of cells and then during the pregnancy the whole organ the uterus has to increase in mass therefore it increases the cell division in this organ.

And the same for the breast. The breast has to grow in order to produce milk after the baby has been born therefore the estrogen induces the growth of these cells also. And cancer starts with cell growth but normally the cells know where to stop to grow but sometimes they get a hit mutation and then they don't know when to stop and compounds which induce growth of the cells can help cancer cells to form tumors and that's why the estrogen increases the cancer rates in these organs because one of it's rule is to induce growth in the uterus and in the breast cells. And what else it does is in the liver for example it induces the synthesis of the special protein angiotenzene which is used to regulate the blood pressure and many other things. It also regulates the processes in the brain for to control your mood. So therefore if there a vistral so estrogen makes women feel good because they have to have positive mood to get baby and if there is a vistral of the estrogen they often have depression. And also in men estrogen has some activity it is not a pure female hormone so men do also have estrogen. Not the high concentrations and after menopause women level down to the concentration of estrogen which men have. So then the difference disappears.

Men are normally not treated with synthetic estrogens only if they have prostate cancer and so because the what prostate so the testosterone in men does the same with the same with the prostate cells so with men sexual functions what estrogen does with women sexual functions and especially the testosterone increases the cell growth of the prostate and if there are malignant cells single malignant cells and there is a high level of testosterone then these can outgrow to a tumor and give prostate cancer and to the testosterone and the estrogen are antagonists and you treat men with estrogen then it antagonizes the testosterone and reduces the growth of prostatic cells. And that's the reason why men with prostate cancer are treated with estrogen. But at the same time they start to convert to female types so their breasts are growing and they beard does not grow anymore so a lot of symptoms which men do not like but the vital estrogens do not give these symptoms because they are reacting. So with vital estrogens men do not experience any loss of sexual functions or any change in their phenotype. On the other hand vital estrogens could never reduce the growth of prostatic cells and reduce the risk of getting prostate cancer that could be another benefit of vital estrogens expressed in men.

Test substance TNCONC was evaluated for possible Estrogenic Agonism in ICR derived female immature mice at a maximum tolerated dose of 4000 mg/kg administered orally once daily for 3 consecutive days. Significant estrogenic agonism activity, as manifested by change in wet weight of the uterus, was observed for TNCONC (50% increase relative to vehicle treated group). Each of the test animals exhibited enlarged intestinal tracts; however, no behavioral changes were observed during the testing period. It is concluded that TNCONC at 4000 mg/kg P0 demonstrated significant estogenic agonism activity in mice.

The following related to the materials and equipment:

1. Test Substances and Dosing Pattern—TNCONC, provided by Morinda, Inc., was dissolved in 2% Tween 80/0.9% NaCl. For testing, a maximum tolerated dose of 4000 mg/kg was administered intraperitoneally daily for 3 consecutive days, and a dosing volume of 10 ml/kg was used.

2. Animals—Female ICR mice provided by MDS Pharma Services—Taiwan Ltd. were used. Space allocation for 5 animals was 29×18×13 cm. Animals were housed in APEC$^R$ cages and maintained in a controlled temperature (22° C.-24° C.) and humidity (60%-80%) environment with 12 hours light dark cycles for at least one week in MDS Pharma Services—Taiwan Laboratory prior to use. Free access to standard lab chow for rats (Lab Diet, Rodent Diet, PMI Nutrition International, USA) and tap water was granted. All aspects of this work including housing, experimentation and disposal of animals were performed in general accordance with the International Guiding Principles for Biomedical Research Involving Animals (CIOMS Publication No. ISBN 92 90360194, 1985), 3. Chemicals—β-Estradiol 3-Benzoate (Sigma, USA), Pyrogen Free Salin (Sinton, Taiwan) and Tween 80 (Wako, Japan).

4. Equipment—Animal case (ShinTech, R.O.C.), Electronic scale 0.0001 g-9.9999 g (R16OP, Sarturius, Germany), Glass syringe (1 ml, 0.5 ml Mistuba, Japan), Hypodermic needle (26 G×1", TOP Corporation, Japan), mice oral needle, Stainless scissors (Klappnecker, Germany).

Test substance was administered at a maximum tolerated dose of 4000 mg/kg IP for three consecutive days to a group of 5 ICR derived immature female mice weighing 13±1 g. The animals were sacrificed 24 hours after the final dose and wet weight of the uterus of each animal was measured. A 50 percent or more ($\geqq$50%) increase in uterine wet weight relative to control group of animals indicates possible estrogen agonist activity. The following tables provide the results of the research performed:

TABLE 1

Protocol # 531000 Estrogenic Agonism in Mice

| Treatment | Route | Dose | N | Weight (mg) of Uterus Individual | Average | % Increase |
|---|---|---|---|---|---|---|
| Vehicle (2% Tween 80/0.9% NaCl) | IP | 10 ml/kg | 1 | 14.9 | 15.7 | — |
| | | | 2 | 16.1 | | |
| | | | 3 | 14.7 | | |
| | | | 4 | 18.0 | | |
| | | | 5 | 14.6 | | |
| PT# 1026431-ADD (MDA-6) (TNCONC) | IP | 4000 mg/kg | 1 | 23.4 | 23.5 | (50) |
| | | | 2 | 23.5 | | |
| | | | 3 | 27.5 | | |
| | | | 4 | 19.6 | | |
| | | | 5 | 23.5 | | |
| β-Estradiol 3-Benzoate | PO | 0.03 mg/kg | 1 | 28.7 | 30.2 | (83) |
| | | | 2 | 20.7 | | |
| | | | 3 | 31.3 | | |
| | | | 4 | 35.6 | | |
| | | | 5 | 34.9 | | |

A vehicle or test substance was administered IP for three consecutive days to female immature mice weighing 13±1 g. The animals were sacrificed 24 hours after the final dose and wet weight of the uterus of each animal was determined. A 50 percent or more ($\geq 50\%$) increase in uterine wet weight relative to the vehicle treated group of animals, shown in parenthesis, indicates possible estrogen agonist activity. Note: The value of Estradiol treated group was compared with historical vehicle control oral 2% Tween 80 (Uterine wet weight as 16.5 mg).

Therefore, as provided above, a dietary composition or supplement is prepared that includes one or more processed products from the Indian Mulberry plant, scientifically known as *Morinda citrifolia* L. and is used to provide estrogenic effects in the human body.

Inhibiting Estrogen Production

The following describes and features a method and formulation for inhibiting aromatase and for treating and preventing cancerous cell growth within a mammal, as well as for reducing estrogen production in mammals that contributes to the growth of estrogen-dependent cancerous tumors, each through the prophylactic administration of a naturaceutical formulation comprising at least one *Morinda citrifolia* product in processed form.

Embodiments of the present invention advances aromatase inhibitors by providing a naturaceutical composition or aromatase inhibitor or estrogen-dependent cancer cell treatment formulated with *Morinda citrifolia* from the Indian Mulberry plant. The *Morinda citrifolia* is incorporated into various carriers or naturaceutical compositions suitable for in vivo treatment of a patient. For instance, the inhibitor may be ingested, injected, introduced intravenously, or otherwise internalized as is appropriate and directed.

In one exemplary embodiment, the naturaceutical composition of the present invention comprises one or more of a processed *Morinda citrifolia* product present in an amount by weight between about 0.01 and 100 percent by weight, and preferably between 0.01 and 95 percent by weight. Several embodiment of formulations are provided below. However, these are only intended to be exemplary as one ordinarily skilled in the art will recognize other formulations or compositions comprising the processed *Morinda citrifolia* product.

The processed *Morinda citrifolia* product comprises at least one of the active ingredients in the naturaceutical, or contains one or more active ingredients, such as Quercetin and Rutin, and others, for effectuating the inhibition of aromatase and reducing and regulating estrogen production, inhibiting estrogen receptors from binding with estrogen, as well as for effectuating the destruction of estrogen-dependent cancerous cells, particularly early stage estrogen-dependent cancerous cells.

Active ingredients within the processed *Morinda citrifolia* product may be extracted out using various alcohol or alcohol-based solutions, such as methanol, ethanol, and ethyl acetate, and other alcohol-based derivatives using any known process in the art. The active ingredients of Quercetin and Rutin are present in amounts by weight ranging from 0.01-10 percent of the total formulation or composition. These amounts may be concentrated as well into a more potent concentration in which they are present in amounts ranging from 10 to 100 percent.

The processed *Morinda citrifolia* product may be formulated with various other ingredients to produce various compositions, such as a naturaceutical composition, a topical dermal composition, or others. The ingredients to be utilized in a naturaceutical composition are any that are safe for introduction into the body of a mammal, and particularly a human, and may exist in various forms, such as liquids, tablets, lozenges, aqueous or oily solutions, dispersible powders or granules, emulsions, syrups, elixirs, etc. Moreover, since the naturaceutical composition is preferably consumed orally, it may contain one or more agents selected from the group consisting of sweetening agents, flavoring agents, coloring agents, preserving agents, and other medicinal agents as directed.

The ingredients to be utilized in a topical dermal composition are also any that are safe for internalizing into the body of a mammal and may exist in various forms, such as gels, lotions, creams, ointments, etc., each comprising one or more carrier agents. The ingredients for systemically (e.g. intravenously) administered formulations may also comprise any known in the art.

The present invention further features a method of administering a naturaceutical composition to a mammal to inhibit aromatase, as well as to reduce and/or regulate estrogen production. In one exemplary embodiment, the method comprises the steps of (a) formulating a naturaceutical composition comprising in part a processed *Morinda citrifolia* product present in an amount between about 0.01 and 95 percent by weight, wherein the composition also comprises a carrier, such as water or purified water, and may also comprise other natural or artificial ingredients; (b) administering the naturaceutical composition into the body of a mammal, such that the processed *Morinda citrifolia* product is sufficiently internalized; (c) repeating the above steps as often as necessary to provide an effective amount of the processed *Morinda citrifolia* product to inhibit aromatase enzymes that function to convert androgens to estrogens, inhibit receptors from binding with estrogen, and/or reduce and/or regulate estrogen production.

The step of administering the naturaceutical composition into the body preferably comprises ingesting the composition orally through one of several means. Specifically, the naturaceutical composition may be formulated as a liquid, gel, solid, or some other type that would allow the composition to be quickly digested and concentrated within the colon. It is important to note that the step of administering the naturaceutical composition should be carried out in an effective manner so that the greatest concentration of naturaceutical composition is allowed to absorb into the tissues and cells. For the naturaceutical composition to take effect, it must be sufficiently internalized. Once sufficiently internalized, it may then begin to act by inhibiting aromatase, discouraging the binding of estrogen to receptors, and reducing the amount of estrogen produced.

In another embodiment, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition, such as in the mammary region of a breast cancer patient.

In one exemplary embodiment, the naturaceutical composition is administered by taking between 1 teaspoon and 2 oz., and preferably 2 oz., of the naturaceutical composition every two hours each day, or at least twice a day on a continued basis. Also, the naturaceutical composition is to be taken on an empty stomach, meaning at a period of time at least two hours prior to consumption of any food or drink. Following this, the naturaceutical composition is allowed to actively inhibit aromatase, thus positively impacting estrogen-dependent cancerous cells within the body and inhibiting their growth. Of course, one ordinarily skilled in the art will recognize that the amount of composition and frequency of use may vary from individual to individual.

The following tables illustrate or represent some of the preferred formulations or compositions contemplated by the present invention. As stated, these are only intended as exemplary embodiments and are not to be construed as limiting in any way.

| Formulation One | |
| --- | --- |
| Ingredients | Percent by Weight |
| *Morinda citrifolia* puree juice or fruit juice | 100% |

| Formulation Two | |
| --- | --- |
| Ingredients | Percent by Weight |
| *Morinda citrifolia* fruit juice | 85–99.99% |
| Water | 0.1–15% |

| Formulation Three | |
| --- | --- |
| Ingredients | Percent by Weight |
| *Morinda citrifolia* fruit juice | 85–99.99% |
| non-*Morinda citrifolia*-based fruit juices | 0.1–15% |

| Formulation Four | |
| --- | --- |
| Ingredients | Percent by Weight |
| *Morinda citrifolia* fruit juice | 50–90% |
| water | 0.1–50% |
| non-*Morinda citrifolia*-based fruit juices | 0.1–30% |

| Formulation Five | |
| --- | --- |
| Ingredients | Percent by Weight |
| *Morinda citrifolia* puree juice | 85–99.9% |
| water | 0.1–15% |

| Formulation Six | |
| --- | --- |
| Ingredients | Percent by Weight |
| *Morinda citrifolia* puree juice | 85–99.9% |
| non-*Morinda citrifolia*-based fruit juices | 0.1–15% |

| Formulation Seven | |
| --- | --- |
| Ingredients | Percent by Weight |
| *Morinda citrifolia* puree juice | 50–90% |
| water | 0.1–50% |
| non-*Morinda citrifolia*-based fruit juices | 0.1–30% |

| Formulation Eight | |
| --- | --- |
| Ingredients | Percent by Weight |
| *Morinda citrifolia* dietary fiber | 0.1–30% |
| water | 1–99.9% |
| non-*Morinda citrifolia*-based fruit juices | 1–99.9% |

Formulation Nine

| Ingredients | Percent by Weight |
| --- | --- |
| *Morinda citrifolia* dietary fiber | 0.1–30% |
| water | 1–99.9% |
| *Morinda citrifolia* fruit juice or puree juice | 1–99.9% |

Formulation Ten

| Ingredients | Percent by Weight |
| --- | --- |
| *Morinda citrifolia* oil | 0.1–30% |
| carrier medium | 70–99.9% |
| other ingredients | 1–95% |

Formulation Eleven

| Ingredients | Percent by Weight |
| --- | --- |
| *Morinda citrifolia* product | 10–80% |
| carrier medium | 20–90% |

Formulation Twelve

| Ingredients | Percent by Weight |
| --- | --- |
| *Morinda citrifolia* product | 5–80% |
| carrier medium | 20–95% |

Formulation Thirteen

| Ingredients | Percent by Weight |
| --- | --- |
| *Morinda citrifolia* oil or oil extract | 0.1–20% |
| carrier medium | 20–90% |

Formulation Fourteen

| Ingredients | Percent by Weight |
| --- | --- |
| *Morinda citrifolia* puree juice or fruit Juice | 0.1–80% |
| *Morinda citrifolia* oil | 0.1–20% |
| carrier medium | 20–90% |

Formulation Fifteen

| Ingredients | Percent by Weight |
| --- | --- |
| *Morinda citrifolia* puree juice concentrate or fruit juice concentrate | 100% |

Formulation Sixteen

| Ingredients | Percent by Weight |
| --- | --- |
| *Morinda citrifolia* fruit juice concentrate or puree juice concentrate | 85–99.99% |
| Water | 0.1–15% |

As stated, in one exemplary embodiment, the present invention features a method for introducing an internal composition or formulation to inhibit aromatase, reduce/regulate estrogen production, inhibit binding of estrogen to receptors, and treat, prevent, inhibit, destroy, and reverse the effects of estrogen-dependent tumors and cancer cell growth within a cancerous region, such as the mammary region. This method essentially comprises the introduction of an internal composition into the body of a mammal infected with cancerous cells. Several embodiments of the internal composition comprising various different ingredients are contemplated for use herein, with each embodiment comprising one or more forms of a processed *Morinda citrifolia* product as taught and explained herein and a carrier agent or medium.

In one preferred method, aromatase or aromatase enzymes are inhibited, and estrogen-dependent cancer and its growth is treated, prevented, destroyed, and/or reversed, by administering at least one (1) ounce of one of Formulations One through Sixteen above in the morning on an empty stomach, and at least one (1) ounce at night on an empty stomach, just prior to retiring to bed. In one example, which is not meant to be limiting in any way, the beneficial *Morinda Citrifolia* is processed into Tahitian Noni® juice manufactured by Morinda, Incorporated of Orem, Utah.

In one exemplary embodiment, the internal composition comprises the ingredients of: a processed *Morinda citrifolia* product present in an amount by weight between about 10-80 percent; and a carrier medium present in an amount by weight between about 20-90 percent.

In this embodiment, the processed *Morinda citrifolia* product may comprise one or more of a processed *Morinda citrifolia* fruit juice, processed *Morinda citrifolia* puree juice, processed *Morinda citrifolia* dietary fiber, and/or processed *Morinda citrifolia* oil extract product.

In another exemplary embodiment, the internal composition comprises the ingredients of: processed *Morinda citrifolia* fruit juice or puree juice present in an amount by weight between about 0.1-80 percent; processed *Morinda citrifolia* oil present in an amount by weight between about 0.1-20 percent; and a carrier medium present in an amount by weight between about 20-90 percent. *Morinda citrifolia* puree juice or fruit juice may also be formulated with a processed *Morinda citrifolia* dietary fiber product present in similar concentrations.

According to the present invention, the particular methods of introducing an internal composition may comprises any method of actually introducing the internal composition into the body of a mammal for the purposes identified herein. Although the particular methods are many, the present invention recognizes that the internal composition may be introduced intravenously, transdermally, orally, or systemically. No matter what method is employed, it is important to thoroughly internalize the composition so that the internal composition, and particularly the *Morinda citrifolia* and other active ingredients, can effectively inhibit aromatase and treat any estrogen-dependent cancer, thus contributing to the abatement and subsequent inhibition and prevention of such cancer, and also so that any early stage estrogen-dependent cancerous cells can be destroyed.

The carrier medium identified in the above Formulations may comprise any ingredient capable of being introduced into the body of a mammal, and that is also capable of providing the carrying medium to the processed *Morinda citrifolia* product. Specific carrier mediums formulations are well known in the art and not described in detail herein. The purpose of the carrier medium is as stated, to provide a means to embody the processed *Morinda citrifolia* product within the internal composition that is capable of being introduced into the body.

The following examples set forth and present the preventative and treatment effects of the processed *Morinda citrifolia* products on aromatase and estrogen-dependent cancerous cells, as well as the preventative and treatment effects of *Morinda citrifolia* against the proliferation or metastasizing of these cancerous cells. These examples are not intended to be limiting in any way, but are merely illustrative of the benefits and advantageous, as well as the remedial effects, of the *Morinda citrifolia* products.

Example One

Current prior art treatments available for postmenopausal women with breast cancer comprise treatments for either blocking or inhibiting estrogen receptors or blocking aromatase activity. However, these treatments are unable to accomplish both. Recent experiments were conducted using in-vitro bioassays to evaluate the aromatase enzyme inhibiting and radioligand binding activities of *Morinda citrifolia*, in the form of Tahitian Noni® Puree Juice.

In this experiment, human recombinant cells were used as the sources of estrogen receptors $ER_\alpha$ and $ER_\beta$. Each of the positive control enzymes, diethylstilbestrol aromatase, and CYP450 2C19, were of human origin.

Tahitian Noni® puree juice having a concentration of 1% was first investigated. The results of this test indicated that the active ingredient of *Morinda citrifolia* caused or induced a 89% aromatase inhibition with the CYP450 2C19 enzyme receptor, a 99% aromatase inhibition of the estrogen-alpha enzyme receptors, and a 102% aromatase inhibition of the estrogen-beta enzyme receptors. These results seems to suggest that *Morinda citrifolia* puree juice at the concentration used had a significant impact on the inhibition of aromatase and estrogen receptors, which inhibition compares favorably to current prior art treatments.

Furthermore, it was found that *Morinda citrifolia* inhibited 81% of the 1A2, 89% of the 2C19, 81% of the 2C9, 93% of the 2D6, and 77% of the 3A4 CYP450 enzymes.

Thus, as discussed herein, embodiments of the present invention embrace estrogenic effects in the human body. More particularly, the present invention relates to the utilization of a dietary composition or supplement to selectively inhibit estrogen production and to provide estrogenic effects in the human body, wherein the composition is formulated with one or more processed products from the Indian Mulberry plant, scientifically known as *Morinda citrifolia* L. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for selectively inhibiting estrogen production and providing estrogenic effects, comprising administering to a patient in need thereof, an effective amount of a formulation comprising:
   an alcoholic extract of *Morinda Citrifolia* leaves;
   quercetin and rutin both present between 0.1 and 10 percent of the formulation;
   *Morinda Citrifolia* oil present between 0.1 and 10 percent of the formulation; and
   *Morinda Citrifolia* juice present between 0.1 and 80 percent of the formulation.

2. The method of claim 1, wherein the formulation further comprises:
   juice from a fruit other than *Morinda Citrifolia* present between 1 and 99.9 percent of the formulation.

3. The method of claim 1, wherein the effective amount comprises at least one ounce of the formulation twice a day.

4. The method of claim 1, wherein the formulation comprises a beverage.

5. The method of claim 1, wherein the formulation comprises a transdermal cream.

6. The method of claim 1, wherein the formulation comprises a tablet.

7. The method of claim 1, wherein the formulation comprises a powder.

* * * * *